United States Patent [19]

Harui et al.

[11] Patent Number: 4,543,960

[45] Date of Patent: Oct. 1, 1985

[54] TRANSESOPHAGEAL ECHO CARDIOGRAPHY SCANHEAD

[75] Inventors: Norio Harui, Seattle, Wash.; Jacques Souquet, Meudon, France

[73] Assignee: Advanced Technology Laboratories, Inc., Bothell, Wash.

[21] Appl. No.: 728,445

[22] Filed: May 1, 1985

Related U.S. Application Data

[63] Continuation of Ser. No. 484,003, Apr. 11, 1983, abandoned.

[51] Int. Cl.⁴ .............................................. A61B 10/00
[52] U.S. Cl. ..................................... 128/660; 128/661
[58] Field of Search ............................ 128/660, 661, 4; 73/633, 634

[56] References Cited

U.S. PATENT DOCUMENTS

| | | | |
|---|---|---|---|
| 4,149,419 | 4/1979 | Connell, Jr. et al. | 128/660 |
| 4,272,991 | 6/1981 | Cribbs | 128/660 |
| 4,273,111 | 6/1981 | Tsukaya | 128/660 |
| 4,419,987 | 12/1983 | Ogiu | 128/4 |
| 4,462,408 | 7/1984 | Silverstein et al. | 128/660 |

OTHER PUBLICATIONS

Hisanaga et al. (I), Proceedings of the 23rd Annual Meeting of the Aium 1978, A New Trans-Digestive Tract Scanner with a Gastro-Fiber Scope, p. 108.
Hisanaga et al. (II), Proceedings of the 23rd Annual Meeting of the Aium 1978, A New Transesophagael Real-Time Linear Scanner and Initial Clinical Results, p. 112.

*Primary Examiner*—Kyle L. Howell
*Assistant Examiner*—Ruth S. Smith
*Attorney, Agent, or Firm*—Lawrence S. Levinson; Sanford J. Asman

[57] ABSTRACT

A scanhead for use in ultrasonic echo cardiography is described. The scanhead is particularly adapted for imaging a patient's heart from the patient's esophogus. The scanhead is comprised of a rotating base having a phased array or linear array scanhead mounted thereon, and the scanhead is rotated in order to change the cross-sectional plane of the heart which is intercepted by the ultrasound.

2 Claims, 3 Drawing Figures

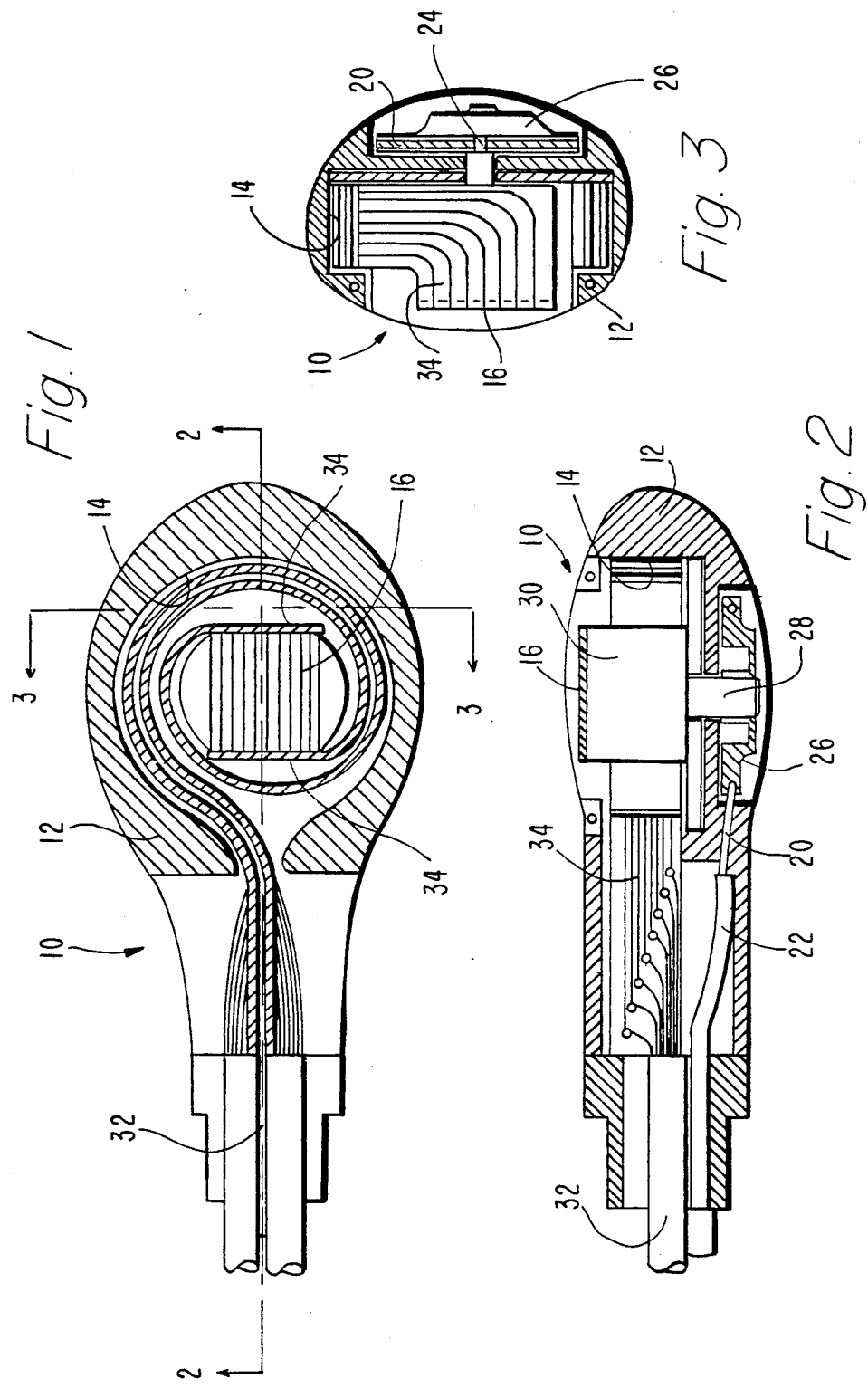

TRANSESOPHAGEAL ECHO CARDIOGRAPHY SCANHEAD

This is a continuation of co-pending application Ser. No. 484,003 filed on Apr. 11, 1983 now abandoned.

BACKGROUND OF THE INVENTION

The present invention relates to a scanhead which is particularly adapted for use in transesophageal echo cardiography applications.

The use of ultrasonic scanners for cardiac studies is well known. A variety of scanheads are used externally in order to obtain real time two dimensional cross-sectional images of various portions of the heart. The standard approach in ultrasonic scanning of the heart is to use a transducer applied to the body at a location in which the heart can be viewed without interference from any intervening bone structures. In particular, this generally means that the transducer is located either between two ribs, or by the neck, or below the sternum. However, it would be desirable to be able to obtain better images of the heart than can be provided from these locations as well as to provide scans of the heart taken along a variety of axes. Accordingly, techniques have been developed whereby ultrasonic scanners are passed down the esophagus of a patient in order to scan the patient's heart from inside the esophagus. This technique is called transesophageal echo cardiography, and it is a particularly useful technique for patients with chronic lung disease, obesity, or abnormal chest wall configurations.

The main disadvantage of this technique is that the examiner has heretofore had minimal control over the transducer position, as the transducer was only connected by a cable to the ultrasonic apparatus.

It would be desirable to have an improved transesophageal echo cardiography (TEEC) scanhead which is capable of providing images of the heart along a variety of axes.

SUMMARY OF THE INVENTION

In accordance with the present invention, a TEEC scanner is provided which is comprised of a pivotally mounted, elongated, multi-element transducer together with means for pivoting the transducer within a housing designed to be passed down the esophagus of a patient.

In accordance with the present invention, an ultrasonic scanhead adapted for use in transesophageal echo cardiography is comprised of a housing having a cylindrical cavity formed in it. There is an elongated, multi-element ultrasonic array mounted on a pulley within the cavity. The scanhead also includes some type of means for rotating the array within the housing, and means which enables an operator to rotate the array within the housing, while the scanhead is in a patient. In addition there is an electrical connection between the scanhead and an external ultrasound unit.

BRIEF DESCRIPTION OF THE DRAWING

In the Drawing:

FIG. 1 is a top cross-sectional view of a transesophageal echo cardiography scanhead in accordance with the present invention;

FIG. 2 is a cross-sectional view of the scanhead of FIG. 1 taken along the line 2—2 of FIG. 1; and FIG. 3 is a cross-sectional view of the scanhead of FIG. 1 taken along the line 3—3 of FIG. 1.

DETAILED DESCRIPTION OF THE PREFERRED EMBODIMENT

Referring now to FIG. 1, a cross-sectional view of the TEEC scanhead 10 of the preferred embodiment of the inventon is shown. In particular, the scanhead 10 comprises a housing 12 having a substantially cylindrical cavity 14 formed therein. Mounted within the cavity 14 is an elongated, multi-element ultrasonic transducer 16. In the preferred embodiment of the invention the transducer 16 is a phased array transducer. However, in specific applications, a linear array transducer might be used without departing from the concept of the present invention.

The scanhead 10 further comprises mechanical means, such as a control cable 20, shown in FIGS. 2 and 3, which is guided through a pair of guide tubes 22 (one of which is visible in FIG. 2) for rotating the transducer 16, whereby the operator of the scanhead 10 can direct and control the angular relationship of the transducer 16 with respect to the housing 12. The control cable 20 is attached to a pulley 26 at a point 24 substantially at the distal end of the pulley 26. The pulley 26 is connected, via shaft 28, to a rotatable base 30 on which the transducer 16 is mounted. Accordingly, it is possible to use the scanhead 10 in a manner whereby cross-sectional views of the heart can be obtained along a variety of orientations. These orientations are selectable by the operator while the operator is actually viewing the patient on the monitor to which the scanhead 10 is connected.

The elements of the transducer 16 are electrically connected to a wire bundle 32 which leads back to a standard scan converter (not shown) via flexible PCB interconnects 34. Accordingly, electrical contact to the transducer 16 is maintained as the transducer 16 is rotated.

As will be obvious to those skilled in the art, various changes to the preferred embodiment of the invention can be made without departing from the spirit or scope of the invention. As a particular example, it would be possible to use a single guide cable with the pulley biased by a spring.

We claim:

1. An ultrasonic scanhead adapted for insertion into the esophagus of a patient for use in transesophageal echo cardiography to produce two-dimensional ultrasound scans of said patient, comprising:
   (a) A housing having a cylindrical cavity formed therein;
   (b) An elongated, multi-element ultrasonic array, said array being comprised of a number of elongated piezoelectric elements having emitting surfaces arranged in a plane, said array having a scan axis which is perpendicular to the long axis of said elements, said array being mounted on a pulley within said cavity;
   (c) Means for rotating said pulley within said housing, whereby said array will be rotated relative to said housing and in the plane of said elements around the axis of rotation of said pulley;
   (d) Means adapted for connecting said means for rotating to an operator control remote from said housing; and
   (e) Means for electrically connecting said array to an external ultrasound unit.

2. The ultrasonic scanhead of claim 1 wherein said means adapted for connecting said means for rotating comprises a pair of guide tubes containing a cable connected to said pulley whereby pulling on one end of said cable rotates said array.

* * * * *